(12) United States Patent
Kobayashi et al.

(10) Patent No.: US 7,605,285 B2
(45) Date of Patent: Oct. 20, 2009

(54) METHOD AND DEVICE FOR MANUFACTURING DIMETHYL CARBONATE

(75) Inventors: Kazuto Kobayashi, Hiroshima (JP); Hiroyuki Osora, Hiroshima (JP); Yoshio Seiki, Hiroshima (JP); Masaki Iijima, Mihara (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 541 days.

(21) Appl. No.: 10/553,009

(22) PCT Filed: Apr. 16, 2004

(86) PCT No.: PCT/JP2004/005477

§ 371 (c)(1), (2), (4) Date: Aug. 21, 2006

(87) PCT Pub. No.: WO2004/092109

PCT Pub. Date: Oct. 28, 2004

(65) Prior Publication Data

US 2007/0037998 A1    Feb. 15, 2007

(30) Foreign Application Priority Data

Apr. 18, 2003    (JP) .............................. 2003-114635

(51) Int. Cl.
C07C 69/96    (2006.01)
(52) U.S. Cl. ....................................... 558/277; 518/726
(58) Field of Classification Search ................. None
See application file for complete search history.

(56) References Cited

U.S. PATENT DOCUMENTS

| | | | |
|---|---|---|---|
| 5,183,920 A | 2/1993 | Myers | |
| 6,894,080 B2 | 5/2005 | Seiki et al. | |
| 2002/0040067 A1 | 4/2002 | Kobayashi et al. | |
| 2003/0032844 A1 | 2/2003 | Seiki et al. | |

FOREIGN PATENT DOCUMENTS

| | | |
|---|---|---|
| EP | 1 182 185 A2 | 2/2002 |
| GB | 2 139 224 | 11/1984 |
| JP | 07-224011 | 8/1995 |
| JP | 10-195028 | 7/1998 |
| JP | 11-35526 | 2/1999 |
| JP | 11-80096 | 3/1999 |
| JP | 2001-122811 | 5/2001 |
| JP | 2001-122812 | 5/2001 |
| JP | 2003-034659 | 2/2003 |
| JP | 2003-34659 | 2/2003 |

OTHER PUBLICATIONS

Japanese Office Action mailed Feb. 10, 2009 in Japanese Patent Application No. 2003-114635 w/translation.

*Primary Examiner*—Kamal A Saeed
(74) *Attorney, Agent, or Firm*—Wenderoth, Lind & Ponack, L.L.P.

(57) ABSTRACT

The present invention provides a method and apparatus for producing dimethyl carbonate, wherein carbon dioxide is recovered from combustion exhaust gas of a steam reformer 10 and a boiler; and some of the recovered carbon dioxide is used for methanol synthesis as a raw material for the steam reformer 10, and the remaining carbon dioxide is allowed to react with some of the yielded methanol to synthesize dimethyl carbonate. According to the present invention, $CO_2$, which has conventionally been discharged, is returned to the steam reformer and is used effectively to produce DMC, and also devices for producing methanol and DMC can be simplified.

16 Claims, 6 Drawing Sheets

FIG.6

METHOD AND DEVICE FOR MANUFACTURING DIMETHYL CARBONATE

TECHNICAL FIELD

The present invention relates to a method and apparatus for producing dimethyl carbonate.

BACKGROUND ART

Dimethyl carbonate can be produced, for example, by method 1 and method 2 described below.

(Method 1)

Figure 5:
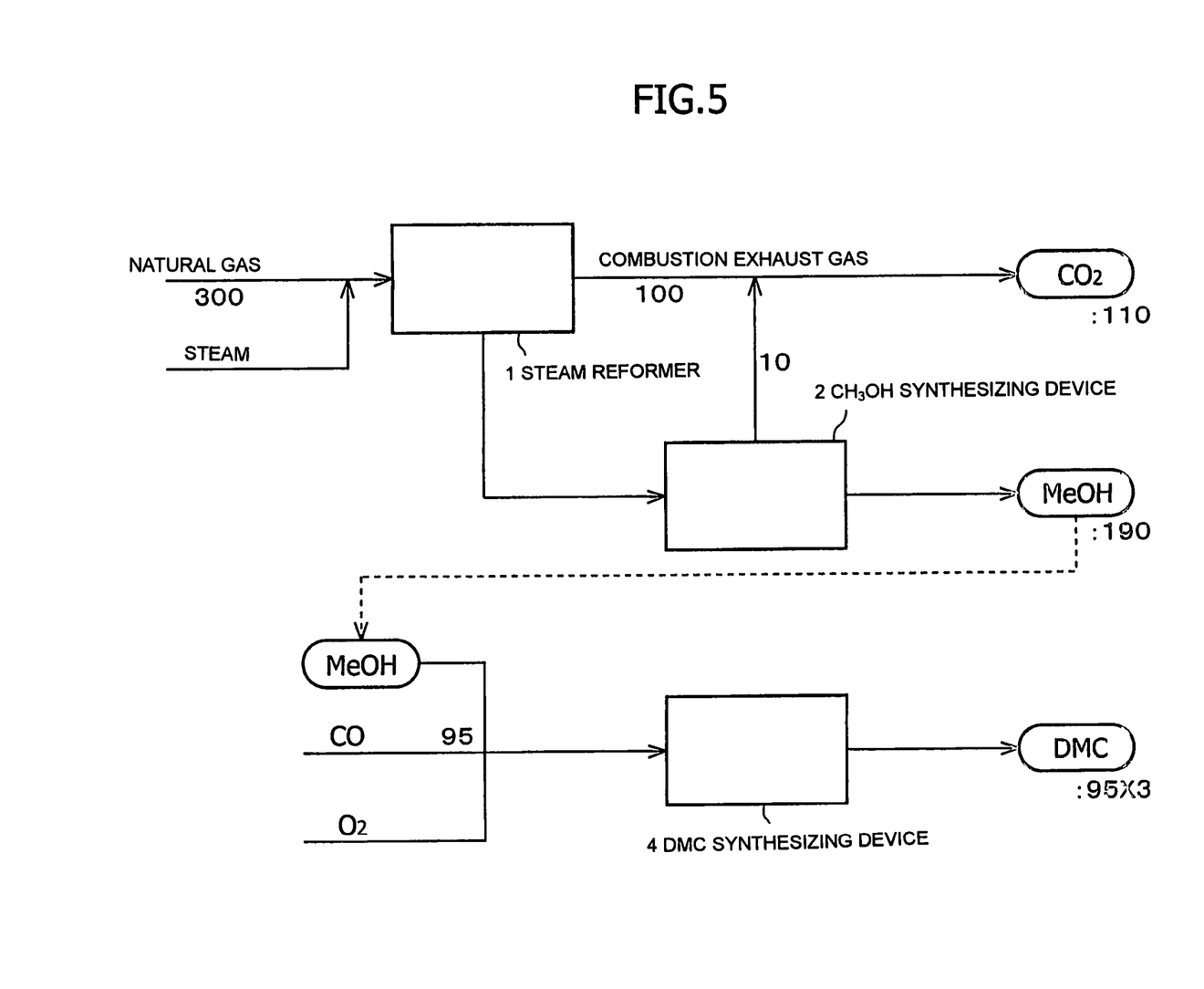
FIG. 5 is a diagram for illustrating a dimethyl carbonate producing method of a steam reformer system in accordance with method 1.

FIG. 5 is a diagram for illustrating method 1 using a steam reformer system. The numerical value noted along each line etc. in FIG. 5 designates a carbon (C) number introduced into a plant or transferred from device to device.

First, natural gas containing steam etc. is steam reformed by an endothermic reaction in a steam reformer 1 to yield a synthesis gas comprising CO, $CO_2$ and $H_2$, and methanol ($CH_3OH$) is synthesized by using this synthesis gas in a methanol synthesizing device 2. At this time, a large quantity of $CO_2$ gas is discharged from combustion exhaust gas of the steam reformer 1 and a boiler, not shown. Next, the synthesized methanol is transported to a dimethyl carbonate (DMC) synthesizing place, where dimethyl carbonate is produced by adding carbon monoxide (CO) and oxygen ($O_2$) to the DMC.

In the case of method 1, for example, if natural gas corresponding to carbon number 300 is used, a synthesis gas containing CO, $CO_2$ and $H_2$ corresponding to carbon number 200 is used to synthesize methanol, and $CO_2$ corresponding to carbon number 100 is discharged as combustion exhaust gas of the steam reformer 1 and the boiler, so that $CO_2$ of carbon number 110 is discharged by adding unreacted $CO_2$ (carbon number 10) from the methanol synthesizing system. Also, in the separate DMC synthesizing place, methanol of carbon number 190 is used for DMC synthesis together with CO and $O_2$, and finally DMC of carbon number 95×3 is produced. In method 1, DMC is produced from methanol by the following reaction:

$$CO+(\tfrac{1}{2})O_2+2CH_3OH \rightarrow CH_3OCOOCH_3+H_2O$$

(Method 2)

Figure 6:
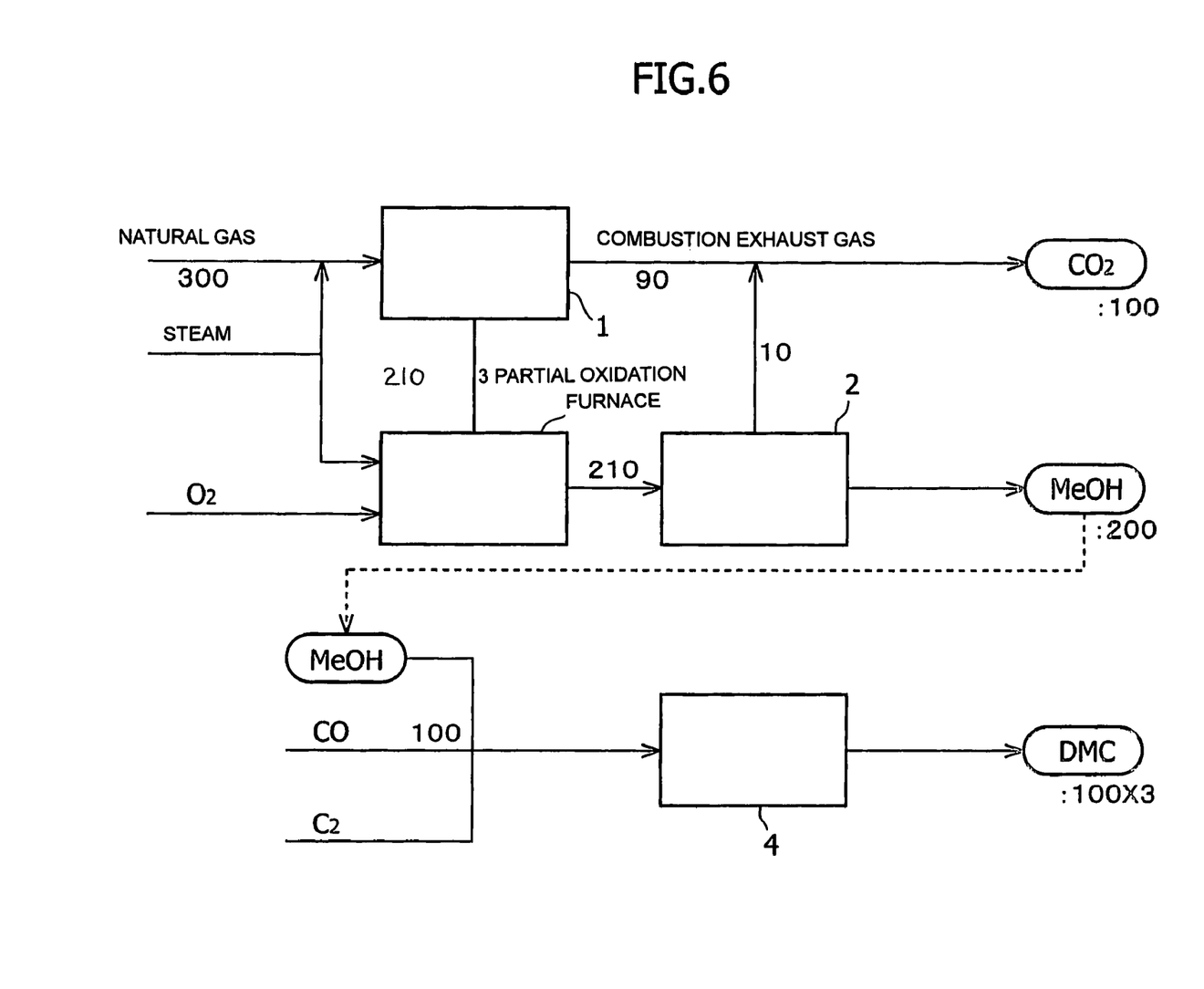
FIG. 6 is a diagram for illustrating a dimethyl carbonate producing method of a steam reformer and partial oxidation system in accordance with method 2.

FIG. 6 is a diagram for illustrating method 2 using a steam reformer plus a partial oxidation system. Compared with method 1, method 2 is characterized in that a partial oxidation furnace 3 is arranged on the upstream side of the methanol synthesizing device 2 and partial oxidation is performed by the oxidation furnace 3 to synthesize methanol.

Also, as a specific method for producing dimethyl carbonate, a technique has been known, for example, in which dimethyl ether and carbon dioxide are allowed to react with each other in the presence of alkali metallic salt and methyl iodide, by which dimethyl carbonate is produced without impairing the activity of catalyst (Japanese Patent Provisional Publication No. 11-80096 (No. 80096/1999)).

DISCLOSURE OF THE INVENTION

In the above-described technique, in producing methanol, the quantity of heat necessary for steam reformation of natural gas is provided by an external heating burner, and also $CO_2$ is discharged in large quantities in addition to exhaust gas of a boiler, not shown. Therefore, this technique has environmental problems. Also, since methanol and DMC are produced at separate places, in producing DMC, the synthesized methanol must be transported to the DMC production place using a vehicle etc. Therefore, the conventional technique has a problem of inferior workability.

The present invention has been made in view of the above circumstances, and accordingly an object thereof is to provide a method and apparatus for producing dimethyl carbonate, in which carbon dioxide is recovered from combustion exhaust gas of a steam reformer and a boiler; some of the recovered carbon dioxide is used for methanol synthesis as a raw material for the steam reformer; and the remaining carbon dioxide is allowed to react with some of the yielded methanol to synthesize dimethyl carbonate; by which $CO_2$, which has conventionally been discharged, is returned to the steam reformer and is used effectively to produce DMC, and also a device for producing methanol and/or DMC can be simplified.

A first aspect of the present invention provides a method for producing dimethyl carbonate in which a synthesis gas mainly consisting of hydrogen, carbon monoxide, and carbon dioxide is synthesized by supplying raw material hydrocarbon and steam to a reformer of an external heating system; methanol is synthesized by allowing the synthesis gas to react over a catalyst; and dimethyl carbonate is produced by adding carbon dioxide to the methanol, characterized in that carbon dioxide in combustion exhaust gas discharged from a combustion radiation section for heating a reaction tube of the reformer is recovered; some or all of the recovered carbon dioxide is mixed in the raw material hydrocarbon to synthesize methanol; and all or some of the remaining carbon dioxide is added to the synthesized methanol to synthesize dimethyl carbonate.

A second aspect of the present invention provides an apparatus for producing dimethyl carbonate, comprising:

a reformer of an external heating system including a steam reforming reaction tube and a combustion radiation section arranged around the reaction tube, which synthesizes a synthesis gas containing carbon monoxide and carbon dioxide by supplying raw material hydrocarbon and steam;

a methanol synthesizing means for synthesizing methanol by allowing the synthesis gas to react over a catalyst; and a dimethyl carbonate producing means for producing dimethyl carbonate by adding carbon dioxide to the synthesized methanol, wherein the apparatus for producing dimethyl carbonate comprises:

a carbon dioxide recovering device for recovering carbon dioxide in combustion exhaust gas discharged from the combustion radiation section of the reformer;

a mixing means of the recovered carbon dioxide in the raw material hydrocarbon, in which some or all of the recovered carbon dioxide is mixed in the raw material hydrocarbon to synthesize methanol; and a mixing means of the recovered carbon dioxide in methanol, in which all or some of the remaining carbon dioxide is added to the synthesized methanol to synthesize dimethyl carbonate.

Hereunder, the present invention is explained in more detail with reference to an embodiment. The scope of the present invention is not restricted by this embodiment.

In the figures, reference numeral 10 denotes a steam reformer, 11 denotes a reaction tube, 12 denotes a combustion radiation section, 13 denotes a convection section, 14 denotes a $CO_2$ recovering device, 15 and 17 denote a compressor, 16, 18 and 20 denote a pipe, 19 denotes a partial oxidation furnace, 21 denotes a stack, and 22 denotes a burner, respectively.

BEST MODE FOR CARRYING-OUT THE INVENTION

A specific embodiment of a dimethyl carbonate producing method in accordance with the present invention will now be described with reference to the accompanying drawings.

The present invention has been made by focusing attention on $CO_2$ in combustion exhaust gas which has been discharged conventionally from both a steam reformer and a boiler, and by focusing attention on the fact that methanol and dimethyl carbonate have conventionally been produced by two independent systems. Specifically, in the present invention, $CO_2$ is utilized effectively by recovering all $CO_2$; some of which is returned to the steam reformer, while the remaining $CO_2$ is utilized for dimethyl carbonate synthesis. Further, in the present invention at least one of methanol and dimethyl carbonate is produced by one system by utilizing the fact that dimethyl carbonate is synthesized based on methanol.

In the present invention, it is preferable that the synthesized synthesis gas be partially oxidized by a partial oxidation furnace, and then methanol be synthesized over a catalyst. By this treatment, the quantity of oxygen introduced into the partial oxidation furnace can be saved corresponding to the quantity of the recovered $CO_2$.

In the present invention, it is preferable that carbon dioxide used for at least one of the methanol synthesis and the dimethyl carbonate synthesis be carbon dioxide recovered from combustion exhaust gas discharged from a combustion radiation section for heating a reaction tube of the reformer and/or carbon dioxide recovered from combustion exhaust gas discharged from a boiler for producing steam used for synthesis of the synthesis gas or a boiler for producing steam used for a steam turbine for a compressor for compressing the carbon dioxide, namely, a boiler existing in the system. By doing this, carbon dioxide in combustion exhaust gas discharged from the boiler in the system can be used effectively in the system as a valuable substance, and moreover the quantity of carbon dioxide released into the atmosphere is reduced significantly. Therefore, this method can contribute greatly to global environmental conservation from the viewpoint of prevention of global warming.

In the present invention, it is preferable that carbon dioxide used for at least one of the methanol synthesis and the dimethyl carbonate synthesis be carbon dioxide recovered from combustion exhaust gas discharged from an exhaust heat recovery section for heating the reaction tube of the reformer and/or carbon dioxide sent from the outside of the system. Thereby, carbon dioxide can be utilized effectively.

In the present invention, it is preferable that some of the synthesized methanol be used for the dimethyl carbonate synthesis, and some thereof be left as it is, by which methanol and dimethyl carbonate be produced at the same time.

In the present invention, methanol and dimethyl carbonate can be produced by appropriately changing the production ratio between methanol and dimethyl carbonate. Therefore, the production volumes of methanol and dimethyl carbonate can be adjusted according to the demands: for example, only methanol can be produced, or both of methanol and dimethyl carbonate can be produced.

In an apparatus for producing dimethyl carbonate in accordance with the present invention, it is preferable that there be provided a carbon dioxide recovering device for recovering carbon dioxide from combustion exhaust gas discharged from the boiler in the system, and further a carbon dioxide supplying means for supplying the carbon dioxide recovered from combustion exhaust gas discharged from the boiler to use the carbon dioxide for at least one of the methanol synthesis and the dimethyl carbonate synthesis.

In the above-described apparatus for producing dimethyl carbonate, it is preferable that there be further provided a carbon dioxide supplying means for supplying carbon dioxide, which is received from the outside of the system, to the methanol synthesizing means and/or the dimethyl carbonate synthesizing means.

In the above-described apparatus for producing dimethyl carbonate, the methanol synthesizing means preferably includes an out-of-system sending means for sending methanol to the outside of the system and an in-system sending means for sending methanol to the dimethyl carbonate synthesizing means.

The present invention offers the following advantages:

(1) Since all $CO_2$, which has been discharged conventionally, is recovered, some of the $CO_2$ being returned to the steam reformer 11, and the remaining $CO_2$ being used to produce DMC, $CO_2$ can be utilized effectively, and hence the raw material cost in the production cost of DMC can be saved.

(2) Since $H_2$ in offgas including CO, $CO_2$ and $H_2$ can be used as a raw material for methanol synthesis, the offgas can be utilized effectively.

(3) Since methanol and DMC are not produced in two plants at separate places in contrast to the conventional example, being produced in one plant at one place, whereby there is no need for transporting methanol, which is a raw material for DMC, using a vehicle etc. in producing DMC, and also a tank etc. for storing methanol is not needed. Therefore, an apparatus for producing methanol and DMC can be set up with a minimum of piping, so that the apparatus can be simplified.

(4) By adjusting the quantity of methanol used for DMC synthesis, the production volumes of methanol and DMC can be set appropriately according to the demand.

(5) If an oxygen-blowing partial oxidation furnace is used, the quantity of oxygen introduced into the partial oxidation furnace can be saved corresponding to the quantity of the recovered $CO_2$.

According to the present invention described above in detail, carbon dioxide is recovered from combustion exhaust gas of the steam reformer and the boiler, and some of the recovered carbon dioxide is used for the methanol synthesis as a raw material for the steam reformer, and the remaining carbon dioxide is allowed to react with some of the yielded methanol to synthesize dimethyl carbonate. Thereby, there can be provided a method and apparatus for producing dimethyl carbonate in which $CO_2$, which has conventionally been discharged, is returned to the steam reformer and is used effectively to produce DMC, and also devices for producing methanol and DMC can be simplified.

Hereunder, a method for producing dimethyl carbonate in accordance with the present invention is explained in more detail with reference to examples. The present invention is not restricted by these examples.

EXAMPLES

Example 1

Example 1 is explained with reference to FIG. 1. Example 1 is an example in which DMC and methanol are produced at the same time by a steam reformer system. A numerical value noted along each line etc. in FIG. 1 designates a carbon (C) number introduced into a plant or transferred from step to step in the plant.

A steam reformer 10 of an external heating system includes a steam reforming reaction tube 11 in which, for example, a nickel-based catalyst is charged, a combustion radiation section 12 arranged around the reaction tube 11, and a convection section 13. The convection section 13 is connected with a carbon dioxide ($CO_2$) recovering device 14 and a stack 21. Reference numeral 22 in FIG. 1 denotes a burner (combustor).

First, natural gas containing methane etc, is steam reformed by endothermic reaction using steam in the steam reformer 10 to yield a synthesis gas consisting of CO, $CO_2$ and $H_2$, and methanol ($CH_3OH$) is synthesized by using this synthesis gas as a raw material. At this time, a large quantity of $CO_2$ is discharged from combustion exhaust gas of the steam reformer 10 and a boiler, not shown. All of the $CO_2$ is recovered, some of the $CO_2$ being returned to the steam reformer 10 through a pipe 16 by a compressor 15, and the remaining $CO_2$ being used for DMC synthesis after being allowed to pass through a pipe 18 by a compressor 17. On the other hand, dimethyl carbonate is produced by the synthesized methanol and the $CO_2$ sent through the pipe 18.

In the case of example 1, for example, if natural gas corresponding to carbon number 300 is used, the synthesis gas containing CO, $CO_2$ and $H_2$ etc., which corresponds to carbon number 220, is used for methanol synthesis, and on the other hand, natural gas corresponding to carbon number 100 is burned by the burner 22 to form combustion exhaust gas. Of the $CO_2$ recovered by the $CO_2$ recovering device 14, $CO_2$ corresponding to carbon number 20 is returned to the steam reformer 10, and $CO_2$ corresponding to carbon number 90 is used for DMC synthesis. Also, of the synthesized methanol corresponding to carbon number 210, methanol corresponding to carbon number 180 is used for DMC synthesis, and methanol corresponding to carbon number 30 is obtained as methanol itself. The $CO_2$ corresponding to carbon number 10 is combined with the $CO_2$ in the exhaust gas, and $CO_2$ corresponding to total carbon number 110 is recovered. The methanol corresponding to carbon number 180 and the aforementioned $CO_2$ corresponding to carbon number 90 are used for DMC synthesis, and resultantly DMC corresponding to carbon number 90×3 and methanol corresponding to carbon number 30 are produced at the same time. Reaction formulas for the steam reforming reaction (synthesis gas producing reaction) and reactions for producing methanol and DMC in example 1 are as follows:

Steam Reforming Reaction $$CH_4+H_2O \rightarrow CO+3H_2$$

$$CH_4+2H_2O \rightarrow CO_2+4H_2$$

Methanol Synthesis Reaction $$CO+2H_2 \rightarrow CH_3OH$$

$$CO_2+3H_2 \rightarrow CH_3OH+H_2O$$

DMC Synthesis Reaction $$2CH_3OH+CO_2 \rightarrow CH_3OCOOCH_3+H_2O$$

Figure 1:
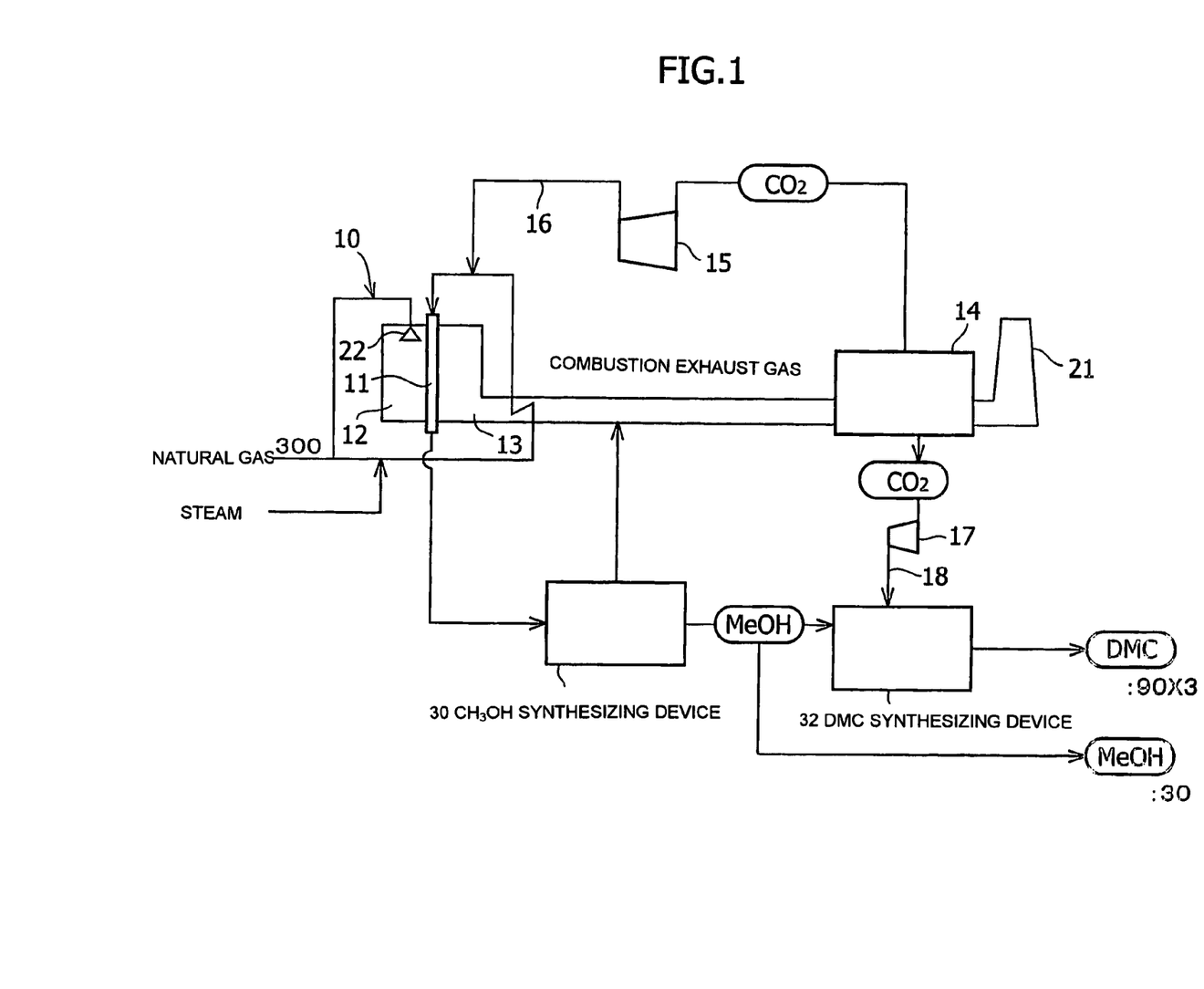
FIG. 1 is a diagram for illustrating a dimethyl carbonate producing method of a steam reformer system in accordance with example 1 of the present invention.

As shown in FIG. 1, an apparatus for producing dimethyl carbonate in accordance with example 1 has a configuration including the steam reformer 10 having the steam reforming reaction tube 11, the combustion radiation section 12 arranged around the reaction tube 11, and the convection section 13, and also including methanol synthesizing means for synthesizing methanol by allowing the synthesis gas mainly consisting of carbon monoxide and carbon dioxide to react over a catalyst; a dimethyl carbonate producing means for producing dimethyl carbonate by adding carbon dioxide to the synthesized methanol; a carbon dioxide recovering device 14 connected to the convection section 13 of the reformer 10 to recover carbon dioxide in combustion exhaust gas discharged from the combustion radiation section 12; means for mixing the recovered carbon dioxide in a source gas, in which some or all of the recovered carbon dioxide is mixed in the source gas to synthesize methanol; and means for mixing the recovered carbon dioxide in methanol, in which all or some of the remaining carbon dioxide is added to the synthesized methanol to synthesize dimethyl carbonate.

The above-described example 1 achieves the following effects:

(1) Since all $CO_2$, which has been discharged conventionally, is recovered, some of the $CO_2$ being returned to the steam reformer 11, and the remaining $CO_2$ being used to produce DMC, $CO_2$ can be utilized effectively, and hence the raw material cost in the production cost of DMC can be saved.

(2) Since methanol and DMC are not produced in two plants at separate places in contrast to the conventional example, being produced in one plant at one place, whereby there is no need for transporting methanol, which is a raw material for DMC, using a vehicle etc. in producing DMC, and also a tank etc. for storing methanol is not needed. Therefore, an apparatus for producing methanol and DMC can be set up with a minimum of piping, so that the apparatus can be simplified.

(3) By adjusting the quantity of methanol used for DMC synthesis, the production volumes of methanol and DMC can be set appropriately according to demand.

Example 2

Example 2 is explained with reference to FIG. 2. Example 2 is an example in which DMC and methanol are produced at the same time by a steam reformer and partial oxidation system. A numerical value noted along a line etc. in FIG. 2 designates a carbon (C) number transferred from step to step in a plant. Also, the same reference numerals are applied to elements that are the same as those in FIG. 1, and the explanation of these elements is omitted.

Figure 2:
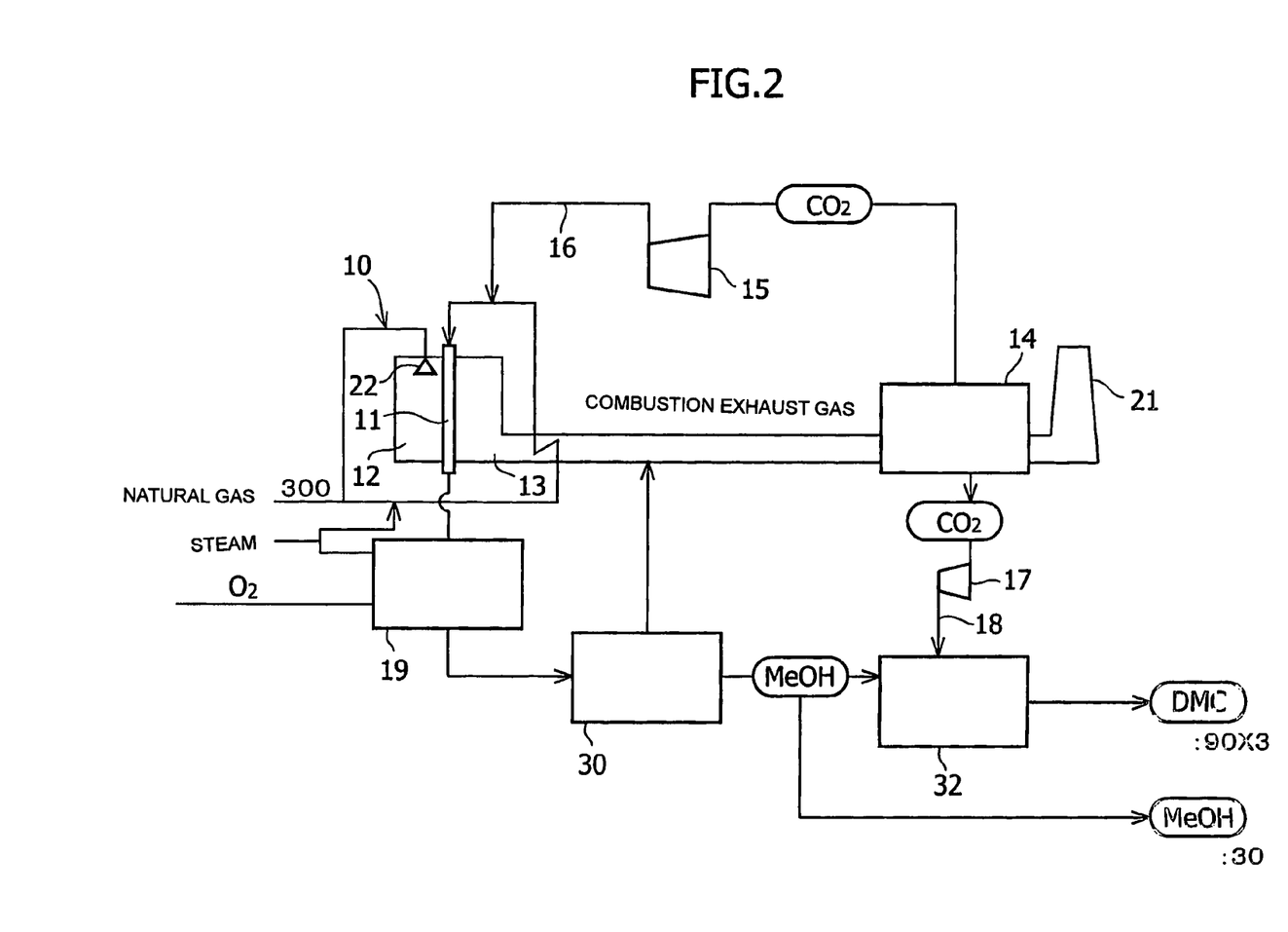
FIG. 2 is a diagram for illustrating a dimethyl carbonate producing method of a steam reformer and partial oxidation system in accordance with example 2 of the present invention.

Reference numeral 19 in FIG. 2 denotes an oxygen-blowing partial oxidation furnace arranged on the upstream side of a methanol synthesizing device, not shown. First, after natural gas such as methane has been steam reformed by endothermic reaction using steam in the steam reformer 10, methanol ($CH_3OH$) is synthesized by using a synthesis gas, which is subjected to partial oxidation in the partial oxidation furnace 19 by using the steam and $O_2$, as a raw material. At this time, a large quantity of $CO_2$ is discharged from combustion exhaust gas of the steam reformer 10 and the boiler, not shown. All of the $CO_2$ is recovered, some of the $CO_2$ being returned to the steam reformer 10 through the pipe 16 by the first compressor 15, and the remaining $CO_2$ being used for DMC synthesis after being allowed to pass through the pipe 18 by the second compressor 17. Also, dimethyl carbonate is produced by the synthesized methanol and the $CO_2$, the $CO_2$ being sent through the pipe 18.

In the case of example 2, for example, if natural gas corresponding to carbon number 300 is used, $H_2$ derived from the synthesis gas corresponding to carbon number 220, which has passed through the partial oxidation furnace 19, is used for methanol synthesis, and also natural gas corresponding to carbon number 90 is burned by the burner 22 to form combustion exhaust gas. Of the $CO_2$ recovered by the $CO_2$ recovering device 14, $CO_2$ corresponding to carbon number 10 is returned to the steam reformer 10, and $CO_2$ corresponding to carbon number 90 is used for DMC synthesis. Also, of the synthesized methanol, methanol corresponding to carbon number 210 is used for DMC synthesis and the recovery of methanol itself, and $CO_2$ corresponding to carbon number 10 is used for recovery. The methanol corresponding to carbon number 180 and the above-mentioned $CO_2$ corresponding to carbon number 90 are used for DMC synthesis, and resultantly DMC corresponding to carbon number 90×3 and methanol corresponding to carbon number 30 are produced at the same time.

The above-described example 2 achieves an effect described below in addition to the effects of items (1), (2) and (3) achieved by example 1. Since partial oxidation is carried out by the partial oxidation furnace 19, as given in Table 1, shown later, the quantity of oxygen necessary for partial oxidation can be decreased to 90 as compared with the case where the quantity of oxygen in the conventional method 2 is taken as 100. Therefore, the quantity of oxygen introduced into the partial oxidation furnace 19 can be saved.

Example 3

Figure 3:
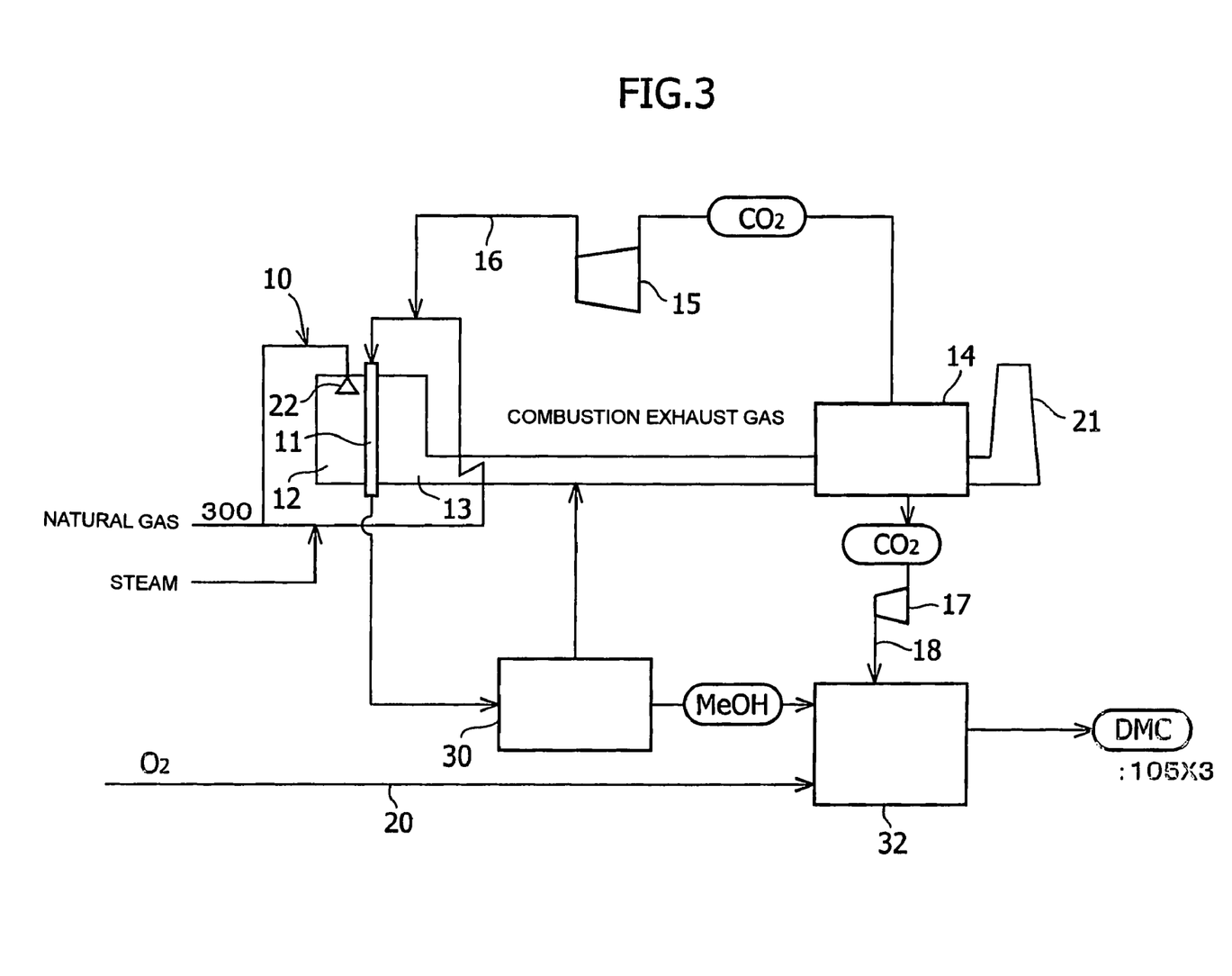
FIG. 3 is a diagram for illustrating a dimethyl carbonate producing method of a steam reformer system in accordance with example 3 of the present invention.

Example 3 is explained with reference to FIG. 3. Example 3 is an example in which only DMC is produced by a steam reformer system. The numerical value noted along each line etc. in FIG. 3 designates a carbon (C) number transferred from step to step in a plant. Also, the same reference numerals are applied to elements that are the same as those in FIG. 1, and the explanation of these elements is omitted.

First, natural gas containing methane etc. is steam reformed by endothermic reaction using steam in the steam reformer 10 to form a synthesis gas, and methanol ($CH_3OH$) is synthesized by using the synthesis gas as a raw material. At this time, a large quantity of $CO_2$ is discharged from combustion exhaust gas of the steam reformer 10 and the boiler, not shown. All of the $CO_2$ is recovered, some of the $CO_2$ being returned to the steam reformer 10 through the pipe 16 by the first compressor 15, and the remaining $CO_2$ being used for DMC synthesis after being allowed to pass through the pipe 18 by the second compressor 17. On the other hand, DMC is produced by all of the synthesized methanol, the $CO_2$ sent through the pipe 18, and $CO_2$ obtained from the outside through a pipe 20.

In the case of example 3, for example, if natural gas corresponding to carbon number 300 is used, the synthesis gas containing CO, $CO_2$ and $H_2$, which corresponds to carbon number 220, is used for methanol synthesis, and also natural gas corresponding to carbon number 100 is burned by the burner 22 to form combustion exhaust gas. Of the $CO_2$ recovered by the $CO_2$ recovering device 14, $CO_2$ corresponding to carbon number 20 is returned to the steam reformer 10, and $CO_2$ corresponding to carbon number 90 is used for DMC synthesis. Also, of the synthesized methanol, methanol corresponding to carbon number 210, the aforementioned $CO_2$ corresponding to carbon number 90, and the $CO_2$ sent from the outside, which corresponds to carbon number 15, are used for DMC synthesis. Resultantly, DMC corresponding to carbon number 105×3 is produced.

According to the above-described example 3, in addition to the effects of items (1) and (2) described in example 1, an effect that excess $CO_2$ discharged in other plants etc. is received and can be utilized effectively can be achieved.

Example 4

Figure 4:
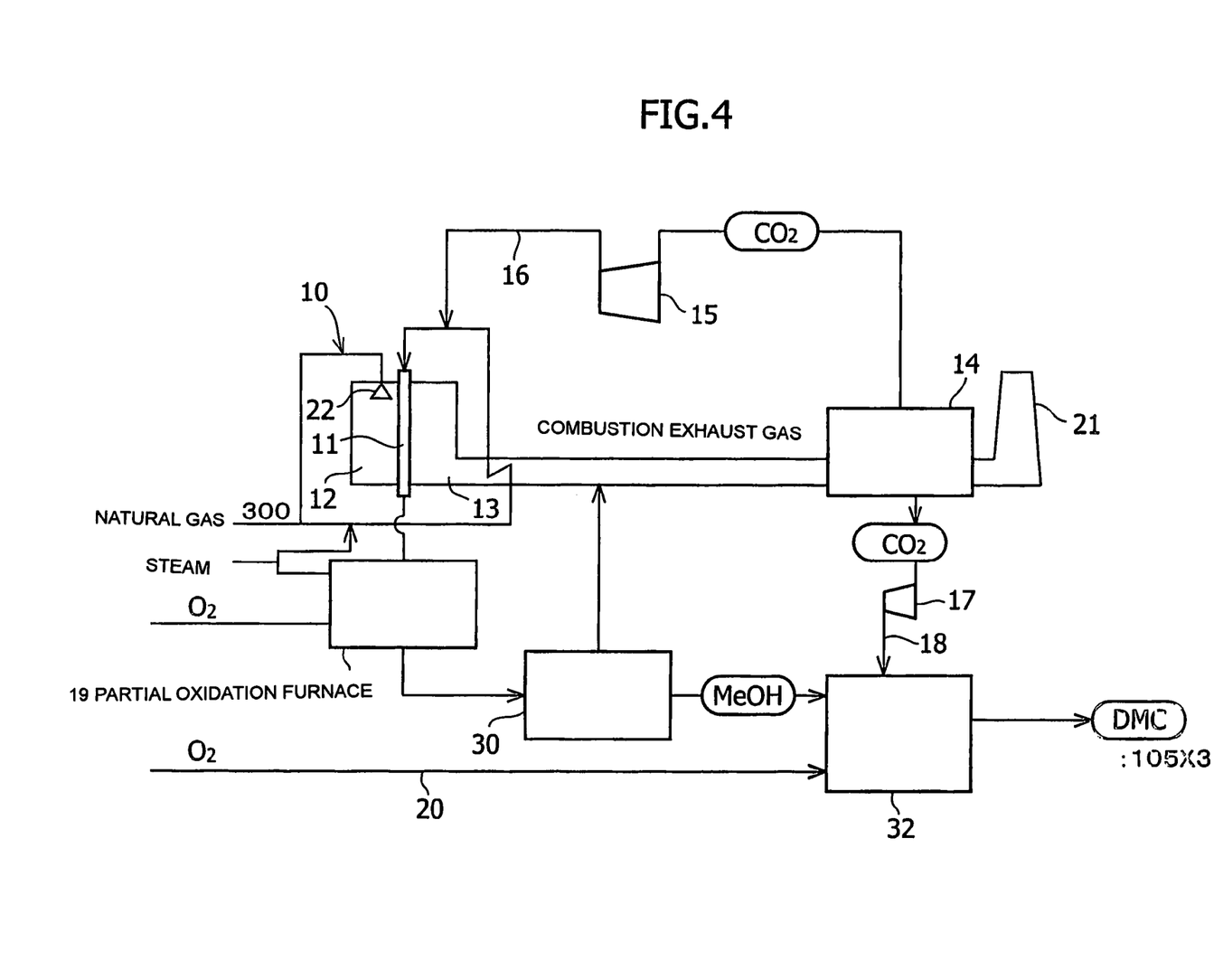
FIG. 4 is a diagram for illustrating a dimethyl carbonate producing method of a steam reformer plus partial oxidation system in accordance with example 4 of the present invention.

Example 4 is explained with reference to FIG. 4. Example 4 is an example in which only DMC is produced by a steam reformer and partial oxidation system. A numerical value noted along each line etc. in FIG. 4 designates a carbon (C) number of a plant. Also, the same reference numerals are applied to elements that are the same as those in FIG. 1, and the explanation of these elements is omitted.

First, after natural gas containing methane etc. has been steam reformed by endothermic reaction using steam in the steam reformer 10, methanol ($CH_3OH$) is synthesized by using a synthesis gas, which is subjected to partial oxidation in the partial oxidation furnace 19 by using the steam and $O_2$, as a raw material. At this time, a large quantity of $CO_2$ is discharged from combustion exhaust gas of the steam reformer 10 and the boiler, not shown. All of the $CO_2$ is recovered, some of the $CO_2$ being returned to the steam reformer 10 through the pipe 16 by the first compressor 15, and the remaining $CO_2$ being used for DMC synthesis after being allowed to pass through the pipe 18 by the second compressor 17. Also, dimethyl carbonate is produced by the synthesized methanol and the $CO_2$ sent through the pipe 18.

In the case of example 4, for example, if natural gas corresponding to carbon number 300 is used, $H_2$ from the synthesis gas corresponding to carbon number 220, which has passed through the partial oxidation furnace 19, is used for methanol synthesis, and also $CO_2$ is recovered from combustion exhaust gas corresponding to carbon number 90. Of the recovered $CO_2$, $CO_2$ corresponding to carbon number 10 is returned to the steam reformer 10, and $CO_2$ corresponding to carbon number 90 is used for DMC synthesis. Of the synthesized methanol, methanol corresponding to carbon number 210, the aforementioned $CO_2$ corresponding to carbon number 90, and $CO_2$ sent from the outside are used for DMC synthesis. Resultantly, DMC corresponding to carbon number 105×3 is produced.

According to the above-described example 4, in addition to the effects of items (1) and (2) described in example 1, an effect that excess $CO_2$ discharged in other plants etc. is received and can be utilized effectively can be achieved. Also, since partial oxidation is carried out by the partial oxidation furnace 19, as given in Table 1, shown later, the quantity of oxygen necessary for partial oxidation can be decreased to 90 as compared with the case where the quantity of oxygen in the conventional method is taken as 100. Therefore, the quantity of oxygen introduced into the partial oxidation furnace 19 can be saved.

Table 1 lists the quantity of discharged $CO_2$, $CO_2$/DMC (mole ratio), and the quantity of oxygen necessary for partial oxidation in conventional methods (1), (2), and examples 1 to 4. In Table 1, $CO_2$/DMC (mole ratio) represents the quantity of discharged $CO_2$ per one mole of product DMC.

TABLE 1

| | | Quantity of discharged $CO_2$, $CO_2$/DMC (mole ratio) | Quantity of oxygen necessary for partial oxidation |
|---|---|---|---|
| Method 1 | Steam reformer (production of DMC) | 1.16 | — |
| Method 2 | Steam reformer (production of DMC) | 1.00 | 100 |
| Example 1 | Steam reformer (production of methanol and DMC) | 0 | — |
| Example 2 | Steam reformer plus partial oxidation (production of methanol and DMC) | 0 | 90 |
| Example 3 | Steam reformer (production of DMC) | −0.14 | — |
| Example 4 | Steam reformer plus partial oxidation (production of DMC) | −0.14 | 90 |

As shown in Table 1, the following are clarified.

(1) $CO_2$/DMC (mole ratio) is $CO_2$/DMC=110/95≈1.16 for method 1 and $CO_2$/DMC=100/100=1.00 for method 2, whereas $CO_2$/DMC (mole ratio) is $CO_2$/DMC=−15/105≈−0.14 (since $CO_2$ is introduced from the outside, the minus sign is used) for example 3 and example 4.

(2) For example 2 and example 4, the quantity of oxygen necessary for partial oxidation can be decreased as compared with method 2. Specifically, when the quantity of necessary oxygen in method 2 in which $CO_2$ is not recovered is taken as 100, the quantity of oxygen can be decreased to 90 in example 2 and example 4 because from $CO_2$ recovered from combustion exhaust gas, $CO_2$ corresponding to carbon number 10 is returned to the steam reformer.

The present invention has been explained above with reference to the embodiment and examples of the invention. These embodiment and examples are provided to simplify understanding of the present invention, and do not restrict the scope of the present invention.

The invention claimed is:

1. A method for producing dimethyl carbonate in which a synthesis gas mainly consisting of hydrogen, carbon monoxide, and carbon dioxide is synthesized by supplying raw material hydrocarbon and steam to a reformer of an external heating system; methanol is synthesized by allowing the synthesis gas to react over a catalyst; and dimethyl carbonate is produced by adding carbon dioxide to the methanol, wherein
carbon dioxide in combustion exhaust gas discharged from a combustion radiation section for heating a reaction tube of the reformer is recovered; some or all of the recovered carbon dioxide is mixed in the raw material hydrocarbon to synthesize methanol; and all or some of the remaining carbon dioxide is added to the synthesized methanol to synthesize dimethyl carbonate.

2. The method for producing dimethyl carbonate according to claim 1, wherein
the synthesized synthesis gas is partially oxidized by a partial oxidation furnace, and then methanol is synthesized over a catalyst.

3. The method for producing dimethyl carbonate according to claim 1, wherein
carbon dioxide used for at least one of the methanol synthesis and the dimethyl carbonate synthesis is carbon dioxide recovered from combustion exhaust gas discharged from the combustion radiation section for heating the reaction tube of the reformer and/or carbon dioxide recovered from combustion exhaust gas discharged from a boiler existing in the system.

4. The method for producing dimethyl carbonate according to claim 1, wherein
carbon dioxide used for at least one of the methanol synthesis and the dimethyl carbonate synthesis is carbon dioxide recovered from combustion exhaust gas discharged from the combustion radiation section for heating the reaction tube of the reformer and/or carbon dioxide sent from the outside of the system.

5. The method for producing dimethyl carbonate according to claim 1, wherein
some of the synthesized methanol is used for the dimethyl carbonate synthesis, and some thereof is left as it is, by which methanol and dimethyl carbonate are produced at the same time.

6. The method for producing dimethyl carbonate according to claim 5, wherein
methanol and dimethyl carbonate are produced by appropriately changing the production ratio between methanol and dimethyl carbonate.

7. An apparatus for producing dimethyl carbonate, comprising a reformer of an external heating system including a steam reforming reaction tube and a combustion radiation section arranged around the reaction tube, which synthesizes a synthesis gas containing carbon monoxide and carbon dioxide by supplying raw material hydrocarbon and steam; a methanol synthesizing means for synthesizing methanol by allowing the synthesis gas to react over a catalyst; and a dimethyl carbonate producing means for producing dimethyl carbonate by adding carbon dioxide to the synthesized methanol, wherein
the apparatus further comprises a carbon dioxide recovering device for recovering carbon dioxide in combustion exhaust gas discharged from the combustion radiation section of the reformer; a mixing means of the recovered carbon dioxide in the raw material hydrocarbon, in which some or all of the recovered carbon dioxide is mixed in the raw material hydrocarbon to synthesize methanol; and a mixing means of the recovered carbon dioxide in methanol, in which all or some of the remaining carbon dioxide is added to the synthesized methanol to synthesize dimethyl carbonate.

8. The apparatus for producing dimethyl carbonate according to claim 7, wherein
the apparatus further comprises a carbon dioxide recovering device for recovering carbon dioxide from combustion exhaust gas discharged from a boiler in the system, and a carbon dioxide supplying means for supplying the carbon dioxide recovered from combustion exhaust gas discharged from the boiler to use the carbon dioxide for at least one of the methanol synthesis and the dimethyl carbonate synthesis.

9. The apparatus for producing dimethyl carbonate according to claim 7, wherein
the apparatus further comprises a carbon dioxide supplying means for supplying carbon dioxide, which is received from the outside of the system, to the methanol synthesizing means and/or the dimethyl carbonate synthesizing means.

10. The apparatus for producing dimethyl carbonate according to claim 7, wherein
the methanol synthesizing means comprises an out-of-system sending means for sending methanol to the outside of the system and an in-system sending means for sending methanol to the dimethyl carbonate synthesizing means.

11. The method for producing dimethyl carbonate according to claim 2, wherein
carbon dioxide used for at least one of the methanol synthesis and the dimethyl carbonate synthesis is carbon dioxide recovered from combustion exhaust gas discharged from the combustion radiation section for heating the reaction tube of the reformer and/or carbon dioxide recovered from combustion exhaust gas discharged from a boiler existing in the system.

12. The method for producing dimethyl carbonate according to claim 2, wherein
carbon dioxide used for at least one of the methanol synthesis and the dimethyl carbonate synthesis is carbon dioxide recovered from combustion exhaust gas discharged from the combustion radiation section for heating the reaction tube of the reformer and/or carbon dioxide sent from the outside of the system.

13. The method for producing dimethyl carbonate according to claim 2, wherein
some of the synthesized methanol is used for the dimethyl carbonate synthesis, and some thereof is left as it is, by which methanol and dimethyl carbonate are produced at the same time.

14. The method for producing dimethyl carbonate according to claim 13, wherein
methanol and dimethyl carbonate are produced by appropriately changing the production ratio between methanol and dimethyl carbonate.

15. The apparatus for producing dimethyl carbonate according to claim 8, wherein
the apparatus further comprises a carbon dioxide supplying means for supplying carbon dioxide, which is received from the outside of the system, to the methanol synthesizing means and/or the dimethyl carbonate synthesizing means.

16. The apparatus for producing dimethyl carbonate according to claim 8, wherein
the methanol synthesizing means comprises an out-of-system sending means for sending methanol to the outside of the system and an in-system sending means for sending methanol to the dimethyl carbonate synthesizing means.

* * * * *